US009192764B2

(12) United States Patent
Rohrer et al.

(10) Patent No.: US 9,192,764 B2
(45) Date of Patent: *Nov. 24, 2015

(54) APPARATUS FOR TREATING PELVIC FLOOR DISORDERS AND RELATED METHODS OF USE

(71) Applicant: Boston Scientific Scimed, Inc., Maple Grove, MN (US)

(72) Inventors: Mark Rohrer, Blaine, MN (US); Timothy Jackson, Minneapolis, MN (US); Michael Stucky, Shoreview, MN (US); David J. Ternes, Roseville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/509,941

(22) Filed: Oct. 8, 2014

(65) Prior Publication Data

US 2015/0025594 A1 Jan. 22, 2015

Related U.S. Application Data

(63) Continuation of application No. 13/961,302, filed on Aug. 7, 2013, now Pat. No. 8,886,321.

(60) Provisional application No. 61/680,961, filed on Aug. 8, 2012.

(51) Int. Cl.
*A61N 1/00* (2006.01)
*A61N 1/36* (2006.01)
*A61N 1/04* (2006.01)
*A61N 1/372* (2006.01)

(52) U.S. Cl.
CPC .......... *A61N 1/36007* (2013.01); *A61N 1/0408* (2013.01); *A61N 1/37211* (2013.01)

(58) Field of Classification Search
CPC ......... A61N 1/36; A61N 1/08; A61N 1/3606; A61N 1/36017; A61N 1/36003; A61N 1/36007; A61N 1/0514
See application file for complete search history.

(56) References Cited

U.S. PATENT DOCUMENTS

| 2002/0055761 A1 | 5/2002 | Mann et al. | |
| 2003/0195582 A1* | 10/2003 | Mann | 607/30 |
| 2007/0255346 A1* | 11/2007 | Rondoni et al. | 607/59 |

(Continued)

FOREIGN PATENT DOCUMENTS

WO WO 2011/156286 A2 12/2011

OTHER PUBLICATIONS

International Search Report and Written Opinion for corresponding PCT Application No. PCT/US2013/053950 dated Oct. 15, 2013 (13 pages).

*Primary Examiner* — Robert N Wieland
(74) *Attorney, Agent, or Firm* — Bookoff McAndrews, PLLC

(57) ABSTRACT

A method of optimizing the electrical stimulation of a bladder of a patient including selecting a first subset of electrodes from a set of electrodes positioned adjacent to a set of nerves associated with the bladder. The set of electrodes may include one or more electrodes, each of which may be configured to deliver electrical stimulation pulses generated by a stimulator device to the nerves. The method may further include delivering an electrical stimulation pulse through the selected first subset of electrodes and recording at least one parameter of the electrical stimulation pulse after receiving patient feedback.

20 Claims, 13 Drawing Sheets

(56) References Cited

U.S. PATENT DOCUMENTS

| | | | |
|---|---|---|---|
| 2009/0149917 A1* | 6/2009 | Whitehurst et al. | 607/59 |
| 2010/0161007 A1* | 6/2010 | King | 607/62 |
| 2011/0046697 A1* | 2/2011 | Gerber et al. | 607/59 |
| 2011/0301662 A1 | 12/2011 | Bar-Yoseph et al. | |
| 2012/0101326 A1 | 4/2012 | Simon et al. | |
| 2012/0197338 A1 | 8/2012 | Su et al. | |

* cited by examiner

| ELECTRODES | | | | SENSATION LEVEL | INTOLERABLE LEVEL |
|---|---|---|---|---|---|
| A | C | - | - | 0.4mA | 1.1mA |
| - | A | C | - | 0.5mA | 0.8mA |
| - | - | A | C | 0.9mA | 0.9mA |
| A | - | C | - | 0.3mA | 1.2mA |
| - | - | - | C | 0.8mA | 0.9mA |
| A | A | - | C | 1.1mA | 1.1mA |
| A | - | A | - | 0.5mA | 2.2mA |
| - | C | C | A | 0.8mA | 2.2mA |
| C | A | - | - | 0.6mA | 0.9mA |
| - | A | A | - | 0.6mA | 0.7mA |
| - | - | C | A | 0.8mA | 0.9mA |
| C | - | A | - | 0.6mA | 1.1mA |
| - | C | - | A | 1.0mA | 1.1mA |
| C | - | - | A | 0.1mA | 0.2mA |
| A | C | C | A | 1.0mA | 1.8mA |
| OTHERS | | | | NR | NR |

*FIG. 6*

| ELECTRODES | | | STIMULATION LEVEL | PATIENT RATING |
|---|---|---|---|---|
| A | C | - | 1.0mA | 3.3 |
| A | - | - | 1.1mA | 2.1 |
| A | C | - | 2.1mA | 4.4 |
| - | A | A | 2.1mA | 4.6 |
| C | A | - | 1.0mA | 2.5 |
| A | C | A | 1.7mA | 4.4 |
| A | C | - | 2.1mA, 8hr ON/16hr OFF | 4.1 |
| - | A | A | 2.1mA, 8hr ON/16hr OFF | 4.8 |
| A | C | - | 2.1mA, 1hr ON/1hr OFF (24hrs) | 4.4 |
| A | C | A | 1.7mA, 8hr ON/16hr OFF | 4.5 |
| - | A | A | 2.1mA, 8hr ON/16hr OFF | 4.8 |

FIG. 9

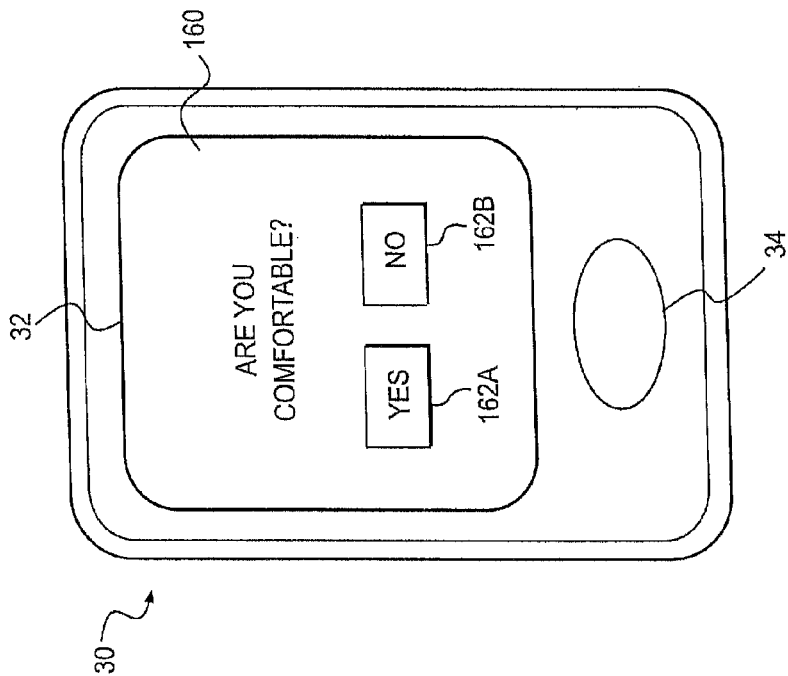
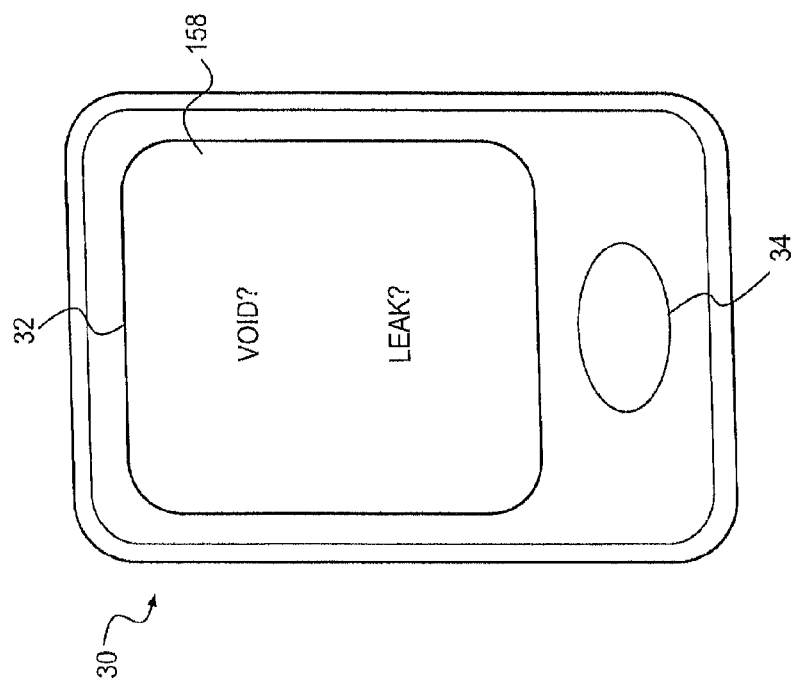

APPARATUS FOR TREATING PELVIC FLOOR DISORDERS AND RELATED METHODS OF USE

PRIORITY

This application is a Continuation Application of U.S. patent application Ser. No. 13/961,302, filed Aug. 7, 2013, now U.S. Pat. No. 8,886,321, which claims the benefit of priority of U.S. Provisional Application No. 61/680,961, filed on Aug. 8, 2012, all of which are incorporated by reference herein in their entireties.

FIELD

The present disclosure relates generally to systems for treating pelvic floor disorders. More particularly, embodiments of the disclosure relate to neuromodulation systems for treating an overactive bladder and methods of optimizing their use.

BACKGROUND

Clinicians use medical devices alone or in combination with drug therapy and surgery to treat medical conditions. Depending on the condition, medical devices can be surgically implanted or connected externally to the patient receiving treatment. For some conditions, medical devices provide the best, and sometimes the only, therapy to restore an individual to a more healthy condition. These conditions may include various pelvic floor disorders such as, for example, overactive bladder (OAB) syndrome.

Overactive bladder (OAB) syndrome is often expressed as frequent and spontaneous activation or inhibition of the detrusor muscle, which may manifest in the form of urge incontinence, urinary frequency syndrome, or chronic urinary retention. Acute conditions, such as, for example, bladder stones, may cause a temporary or "acute" onset of overactive bladder syndrome. Once the stones are passed from the urinary tract, urinary urgency subsides. Chronic conditions such as, for example, interstitial cystitis, may cause persistent overactive bladder syndrome that does not improve with time.

For those with either acute or chronic overactive bladder syndrome who have been unsuccessful with more conservative treatments, such as drugs or behavioral modification, treatments such as neural stimulation can be effective. The neural stimulation treatment procedure is based on mild electrical stimulation of nerves, for example, the sacral nerves and the pudendal nerve, which may inhibit preganglionic neurons, thereby suppressing detrusor overactivity. This treatment employs a neuromodulation system including an implanted lead that is attached to a medical device implanted in the patient receiving treatment. The neural stimulation therapy may be controlled using an external device or may be automated.

While existing neuromodulation systems for treating overactive bladder syndrome may be effective for their intended purpose, it is desirable to improve methods of using such systems so that they may adjust for efficacy and patient tolerance levels to the electrical stimulation. Additionally and/or alternatively, it is desirable to provide a system that may be intuitive to use so that it may be used by patients in an outpatient setting with limited or no medical supervision.

SUMMARY OF THE DISCLOSURE

Embodiments of the present invention are directed to systems and methods for optimizing use of neuromodulation systems for treating a bladder of a patient.

A method of optimizing the electrical stimulation of a bladder of a patient is disclosed. The method may include selecting a first subset of electrodes from a set of electrodes positioned adjacent to nerves associated with the bladder, the set of electrodes including one or more electrodes. The set of electrodes may be configured to deliver electrical stimulation pulses generated by a stimulator device to the nerves. The method may further include delivering at least one electrical stimulation pulse through the first subset of electrodes and recording at least one parameter associated with the at least one electrical stimulation pulse after receiving patient feedback.

In various embodiments, the method may include one or more of the following additional features: wherein receiving patient feedback includes receiving patient feedback in response to a sensation associated with the at least one electrical stimulation pulse; wherein recording the at least one parameter of the at least one electrical stimulation pulse includes recording an amplitude of the at least one electrical stimulation pulse; further including increasing an amplitude of the at least one electrical stimulation pulse until receiving patient feedback based on patient tolerance; further including selecting a second subset of electrodes different from the first subset of electrodes; further including delivering at least one electrical stimulation pulse through the second subset of electrodes; further including recording at least one parameter of the at least one electrical stimulation pulse delivered through the second subset of electrodes after receiving patient feedback; further including comparing the recorded at least one parameter of the at least one electrical stimulation pulse of the first subset of electrodes to the recorded at least one parameter of the at least one electrical stimulation pulse of the second subset of electrodes to determine the relative efficacy of each electrode included in the first subset of electrodes and the second subset of electrodes; further including testing or exhausting all combinations of the electrodes included in the set of electrodes and adjusting delivery of therapy by electrical stimulation to the nerves; wherein delivering at least one electrical stimulation pulse through the first subset of electrodes includes delivering the at least one electrical stimulation pulse for a predetermined period of time; further including determining a level of efficacy of electrical stimulation through the first subset of electrodes over the predetermined period of time based on patient feedback; further including recording the level of efficacy of electrical stimulation for the first subset of electrodes; further including: selecting a second subset of electrodes different from the first subset of electrodes, delivering at least one electrical stimulation pulse through the second subset of electrodes for a predetermined period of time, determining a level of efficacy of electrical stimulation through the second subset of electrodes over the predetermined period of time based on patient feedback, and recording the level of efficacy of electrical stimulation for the second subset of electrodes; further including sensing one or more physiologic signals associated with the bladder; and further including adjusting the level of efficacy based on the one or more physiologic signals.

A method of treating a patient is also disclosed. The method may include delivering therapy by electrical stimulation through a set of electrodes positioned adjacent to nerves associated with a bladder of the patient. The set of electrodes may include one or more electrodes. The electrodes may be configured to deliver electrical stimulation pulses generated by a stimulator device to the nerves. The method may further include receiving data regarding a time of voiding based on patient feedback.

In various embodiments, the method may include one or more of the following additional features: wherein the data includes a date of voiding, and further includes recording the data in a log, such as an electronic voiding log; and further including modifying therapy by electrical stimulation based on the data in the electronic voiding log.

A system for treating a bladder of a patient is also disclosed. The system may include a stimulator device configured to generate electrical stimulation pulses and a set of electrodes coupled to the stimulator device via at least one lead. The set of electrodes may include one or more electrodes. Each electrode included in the set of electrodes is configured to deliver the electrical stimulation pulses to nerves associated with the bladder. The system may further include a controller in communication with the stimulator device. The controller may have a processor configured to (i) cause a selected subset of the set of electrodes to deliver at least one electrical stimulation pulse and (ii) record at least one parameter of the electrical stimulation pulse delivered by the selected subset of electrodes after receiving patient feedback.

In various embodiments, the method may include one or more of the following additional features: wherein the controller is configured to (i) cause a second selected subset of the set of electrodes to deliver at least one stimulation pulse and (ii) record at least one parameter of the electrical stimulation pulse delivered by the second selected subset of the at least one electrode; wherein the controller is configured to receive patient feedback; and wherein the controller is configured to adjust parameters of the electrical stimulation based on the patient feedback.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIG. 6 is a table illustrating the exemplary results captured by the method exemplified in FIG. 4, according to an exemplary embodiment of the disclosure;

FIG. 9 is a table illustrating exemplary results captured by the method exemplified in FIG. 7, according to an exemplary embodiment of the disclosure;

FIG. 13A is a representation of a graphical user interface (GUI) of the receiving device at step 150 of the method illustrated in FIG. 12, according to an exemplary embodiment of the disclosure; and FIG. 13B is a representation of a graphical user interface (GUI) of the receiving device at step 154 of the method illustrated in FIG. 12, according to an exemplary embodiment of the disclosure.

DESCRIPTION OF THE EMBODIMENTS

Reference will now be made in detail to exemplary embodiments of the invention, examples of which are illustrated in the accompanying drawings. Whenever possible, the same reference numbers will be used throughout the drawings to refer to same or like parts.

Generally described, the present disclosure relates to systems and methods for treating pelvic floor disorders. The term "pelvic floor" refers to the group of muscles associated with the pelvic organs (e.g., bladder, rectum, and reproductive organs). Pelvic floor disorders, which are characterized by weakened or injured pelvic muscles, include urinary incontinence, fecal incontinence, and sensory and emptying abnormalities of the urinary tract including bladder overactivity.

Embodiments of the present disclosure relate to methods of optimizing neuromodulation systems for treating bladder overactivity. Bladder overactivity is characterized by involuntary contractions of the detrusor muscle during bladder filling, which may result in a sudden urge to urinate. Neuromodulation systems relate broadly to systems for delivering electrical stimulation to a neural network associated with the bladder for treatment of bladder overactivity. It should be understood that the systems and methods described herein may be used to treat pelvic floor conditions other than bladder overactivity such as, for example, fecal incontinence, chronic idiopathic constipation, interstitial cystitis, and chronic inflammation of the bladder walls. The systems and methods may also be used to treat other conditions of the body, including conditions that require electrical stimulation to treat pressure ulcers (e.g. multiple sclerosis or spinal cord injuries).

Figure 1:
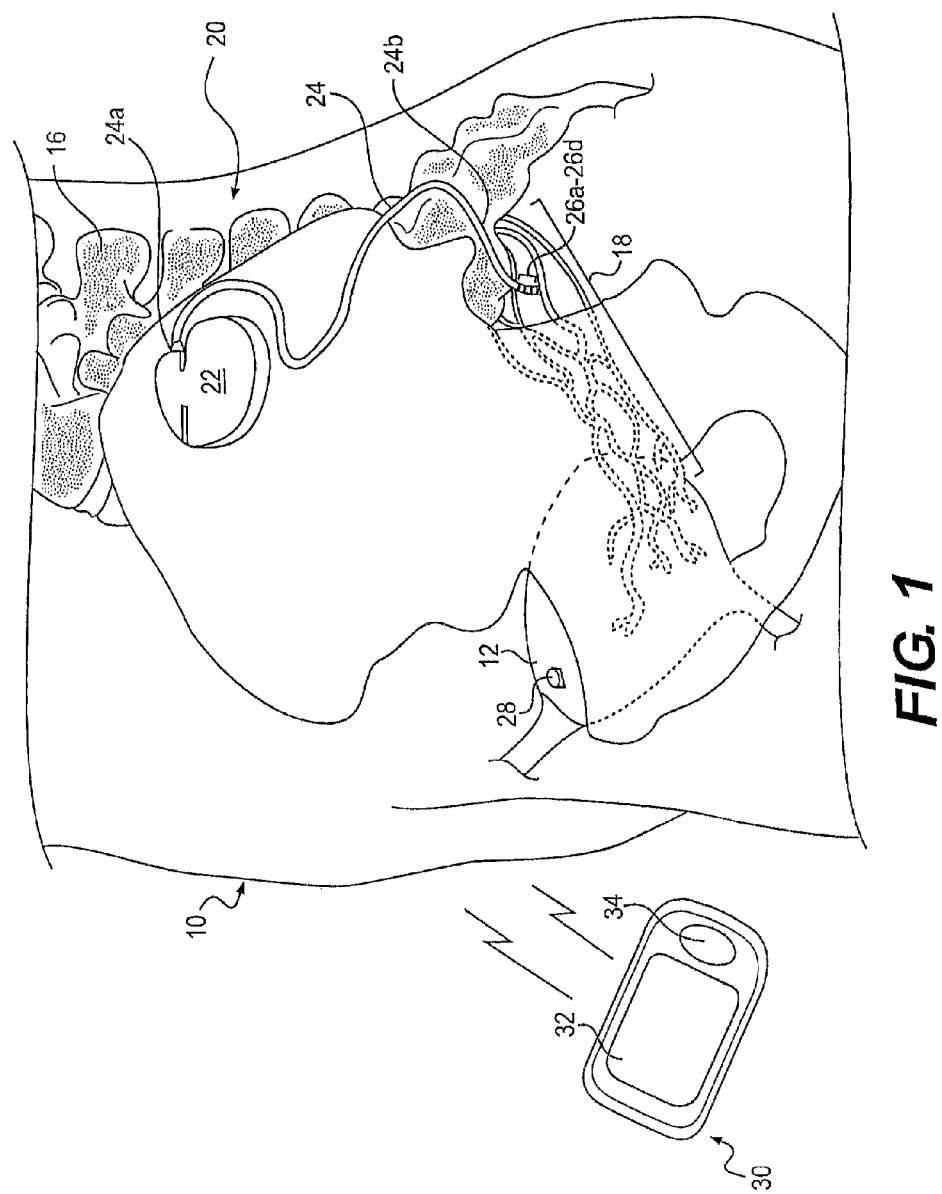
FIG. 1 illustrates a neuromodulation system including an implanted stimulator device and an external receiving device, according to an exemplary embodiment of the present disclosure.

FIG. 1 illustrates an exemplary neuromodulation system 20. System 20 includes an implantable stimulator device 22 that is configured to deliver electrical stimulation therapy to a patient 10. Stimulator device 22 may be an implantable pulse generator and may deliver therapy to patient 10 in the form of electrical stimulation pulses. In the exemplary embodiment, stimulator device 22 is implanted proximate the spine 16 in a region on the posterior hip. Alternatively, stimulator device 22 may be implanted in a more medial tissue region, e.g., in the lower abdomen. As shown in FIG. 1, a proximal end 24a of a lead 24 is electrically coupled to stimulator device 22 in a conventional manner and extends distally from stimulator device 22 towards bladder 12. Distal end 24b of lead 24 may be implanted adjacent to nerves 18 associated with bladder 12 (e.g., sacral nerves). Disposed generally near distal end 24b of lead 24 are a plurality of electrodes 26a-26d. Electrodes 26a-26d may be configured to receive electrical signals indicative of one or more physiological signals and/or deliver electrical stimulation to nerves 18. Although the depicted embodiment includes four electrodes 26a-26d disposed on a distal end 24b of one lead 24, those of ordinary skill in the art will readily recognize that a greater or lesser number of electrodes may be disposed on one or more leads without departing from the scope of the disclosure.

Neuromodulation system 20 may further include a sensing element 28, which may be separate from stimulator device 22. Although the depicted embodiment includes only one sensing element 28, those of ordinary skill in the art will readily recognize that a plurality of sensing elements 28 may be included without departing from the scope of the disclosure. Sensing element 28 may include any suitable sensor known in the art. For example, sensing element 28 may include an electrical, mechanical, or chemical sensor. In one embodiment, sensing element 28 may be placed adjacent to the walls of bladder 12 or within the bladder walls. It will be understood that, as used here, bladder walls include the external or internal walls of bladder 12 so that sensing element 28 may be located inside or outside of bladder 12. Sensing element 28 may be configured to sense one or more physiological signals including, but not limited to, electrical activity, chemical signaling, or biological changes such as, for example, voiding. Sensing element 28 may transmit sensory data via a lead (not shown) and/or wirelessly to stimulator device 22.

Figure 2:
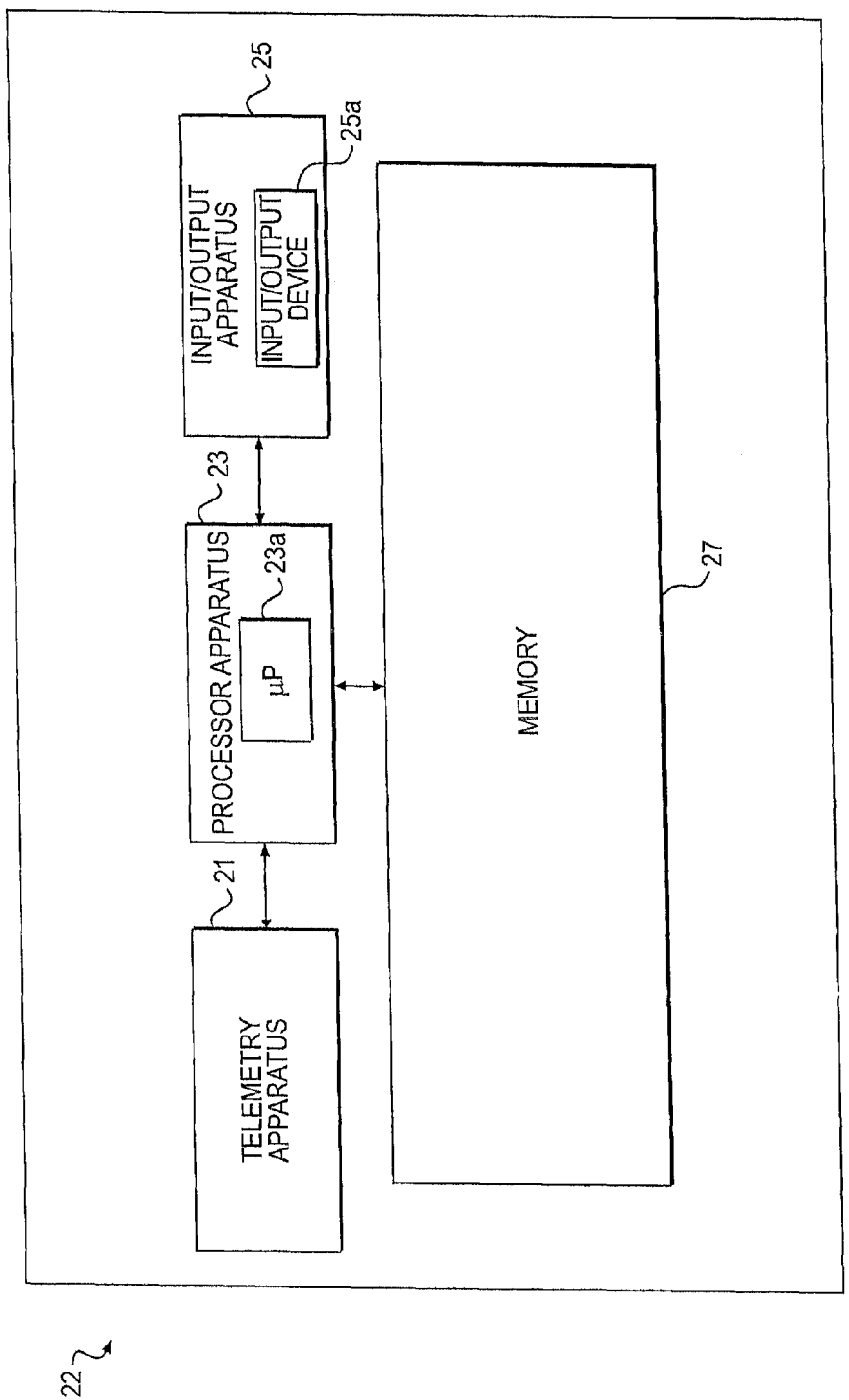
FIG. 2 is a schematic diagram of the stimulator device, according to an exemplary embodiment of the present disclosure.

FIG. 2 is a schematic of stimulator device 22. Stimulator device 22 includes an input/output apparatus 25, a telemetry apparatus 21, and a processor apparatus 23. Input/output apparatus 25 may include at least one input/output device 25a such as, for example, an adapter electrically coupled to proximal end 24a of lead 24. In certain embodiments, sensing element 28 may be connected to stimulator device 22 via a lead (not shown). In those embodiments, input/output apparatus 25 may include an input device (e.g., adapter) electrically coupled to the lead. Telemetry apparatus 21 may be any known device such as, for example, an RF telemetry head, configured to communicate wirelessly with an external receiving device 30. In some embodiments, telemetry apparatus 21 may additionally communicate with sensing element 28. Processor apparatus 23 may include a microprocessor (µP) or any other processor 23a. The processor apparatus 23 may be configured to receive signals from input/output apparatus 25 and/or telemetry apparatus 21. Processor apparatus 23 may be configured to process signals to transmit to receiving device 30 via telemetry apparatus 21 or electrodes 26a-26d via lead 24. In other embodiments, stimulator device 22 may not include a telemetry apparatus 21. For example, neuromodulation may be performed without telemetry apparatus 21 if stimulator device 22 has other sources of electrical contact, signal transmission, or signal processing, for example.

Stimulator device 22 may further include a memory 27. Memory 27 may be any one or more of a variety of types of internal or external storage media, e.g., RAM, ROM, EPROM(s), EEPROM(s), that provide a storage register for data storage, such as in the fashion of an internal storage area of a computer, and can include volatile memory or nonvolatile memory. Memory 27 may be configured to store one or more algorithms and therapeutic programs executable by processor 23 to control delivery of therapy by electrical stimulation. In some embodiments, memory 27 may also store physiologic data received from sensing element 28.

Figure 3:
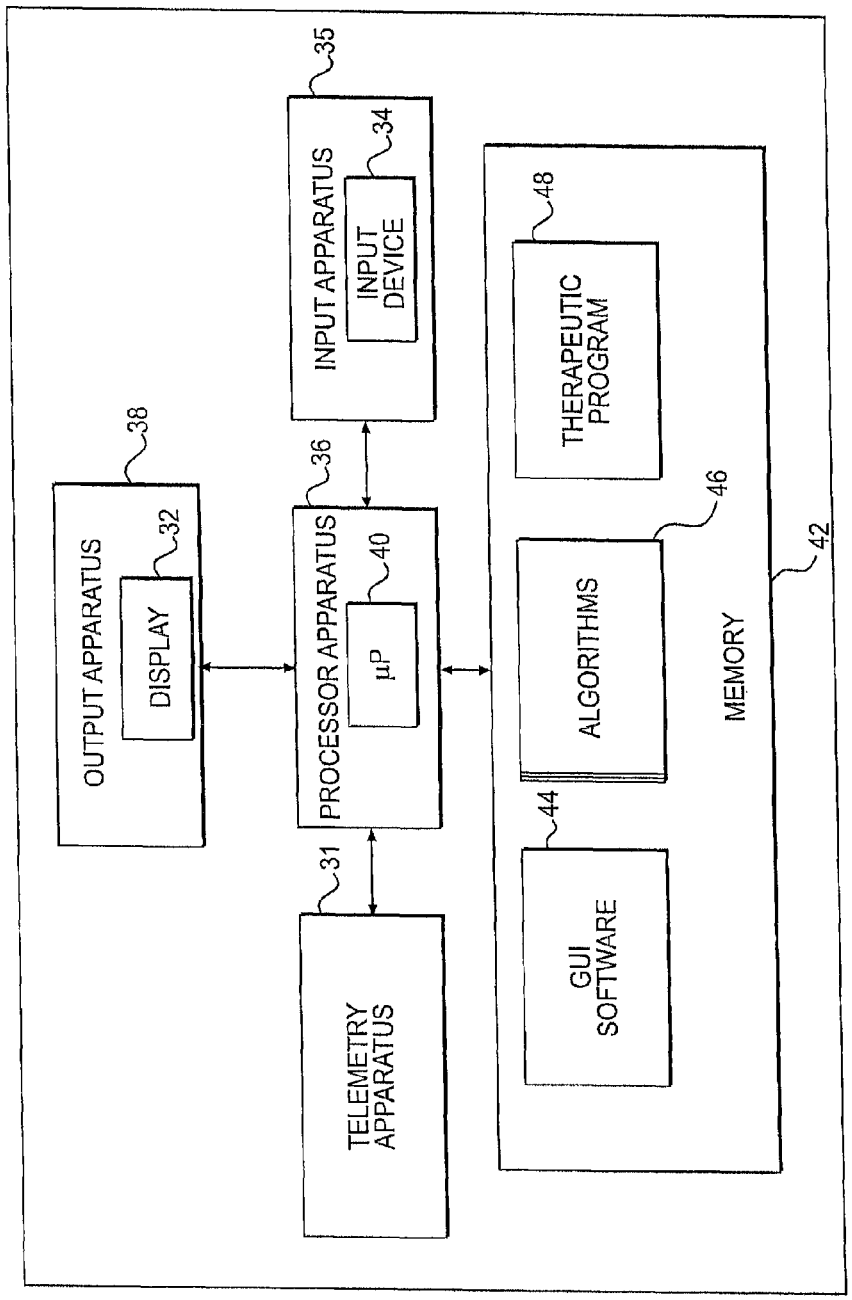
FIG. 3 is a schematic diagram of the receiving device, according to an exemplary embodiment of the present disclosure.

Receiving device 30, as illustrated generally in FIG. 1 and depicted schematically in FIG. 3, may be a handheld electronic control device. Receiving device 30 may be configured to generate control signals and wirelessly transmit those signals to stimulator device 22 to control the therapy by electrical stimulation. In some embodiments, receiving device 30 may be configured to wirelessly receive physiologic data from sensing element 28.

Receiving device 30 may include a telemetry apparatus 31, an input apparatus 35, a processor apparatus 36, and an output apparatus 38. Telemetry apparatus 31 may be any known device such as, for example, an RF telemetry head configured to wirelessly communicate with stimulator device 22 and/or sensing element 28. Input apparatus 35 may include an input device 34 such as, for example, a numeric keypad, a directional keypad, an alphabetic keypad, an alphanumeric keypad, a QWERTY keypad, or any other keypad configuration incorporating one of these layouts or portions thereof. Processor apparatus 36 may include a microprocessor (µP) or any other processor 40. Processor apparatus 36 may be configured to receive input signals from input apparatus 35 and process output signals sent to output apparatus 38 or telemetry apparatus 31. Output apparatus 38 may include a display 32 such as, for example, an LCD display. In some embodiments, display 32 may be a touch screen display.

Receiving device 30 may further include a memory 42. Memory 42 may be any one or more of a variety of types of internal or external storage media such as, without limitation, RAM, ROM, EPROM(s), EEPROM(s), and the like that provide a storage register for data storage, such as in the fashion of an internal storage area of a computer, and may include volatile memory or nonvolatile memory. As a general matter, memory 42 may have stored therein a graphical user interface (GUI) software 44, a therapeutic program 48, and a number of algorithms 46 that are executable on processor 40. GUI software 44 may be executed to display on display 32 one or more prompts requesting input from the patient and/or a third party (e.g., clinician). Program 48 may be executed to control delivery of therapy by electrical stimulation. As will be described below, algorithms 46 may be executed to optimize delivery of therapy by electrical stimulation, adjusting for efficacy and/or individual patient tolerance levels. Additionally and/or alternatively, algorithms 46 may be executed to monitor the efficacy of the therapy over the duration of treatment by recording efficacy observations over time. It is contemplated that at least certain algorithms 46 and/or portions of the algorithms may be stored in memory 27 and executed by processor 23 of stimulator device 22. It is further contemplated that algorithms 46 may be fully-automated, partially-automated, or fully controlled by the patient and/or third party (e.g., clinician). It will be understood that, as used here, clinician refers to any medical personnel having knowledge sufficient to treat and/or assist in the treatment of urinary conditions.

Figure 4:
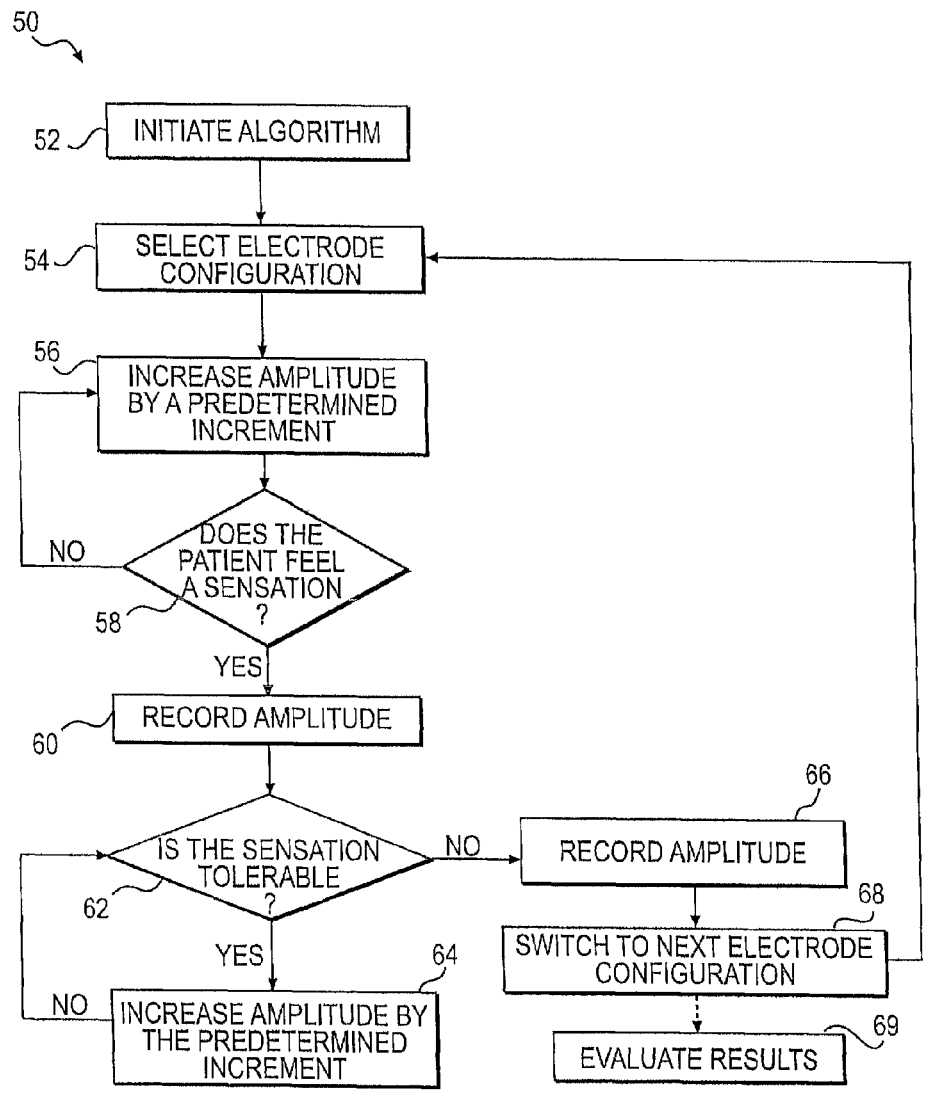
FIG. 4 is a flow diagram illustrating a method of determining an effective electrode configuration for delivery of therapy by electrical stimulation, according to an exemplary embodiment of the disclosure.

FIG. 4 illustrates a method for optimizing delivery of therapy by electrical stimulation. The exemplary method 50 illustrated in FIG. 4 may optimize delivery of therapy by a titration procedure and accordingly adjust therapy parameters such as, for example, an effective electrode configuration. This method may be preferred for patients having an acute overactive bladder condition. However, it is understood that the method may also be used for patients with chronic and/or non-acute overactive bladder conditions. In the exemplary method 50, processor 40 may determine an effective electrode configuration by methodically increasing the amplitude of electrical stimulation pulses delivered by a particular electrode configuration until receiving feedback from the patient or clinician. Processor 40 may then switch to the next electrode configuration in the test until all the configurations have been exhausted. In this manner, the method may eliminate the need for the clinician and/or patient to press "up" or "next" on receiving device 30 during the testing procedure.

As illustrated in FIG. 4, the exemplary method 50 may begin when a corresponding algorithm 46 is initiated (step 52). Algorithm 46 may be initiated at various times over the duration of treatment. For example, algorithm 46 may be initiated after stimulator device 22 has been implanted within the patient's body 10, at a first programming session, or at any subsequent follow-up visit, if appropriate. Algorithm 46 may be initiated at a follow-up visit when, for example, it is believed that the position of one or more of electrodes 26a-26d has changed, when accommodations to the therapy are required, or during any other suitable type of event. In some embodiments, the clinician, either in person or remotely, may initiate algorithm 46. Alternatively, algorithm 46 may be initiated by the patient, for example, under the direction of the clinician.

Upon initiation of algorithm 46 (step 52), an electrode configuration is selected (step 54). Electrode configuration, as used here, refers to a set of one or more electrodes. The electrode configuration may be selected from the plurality of electrodes 26a-26d on lead 24. Each electrode configuration may be distinguished by the number of electrodes and/or, in some embodiments, the polarities of each electrode of the electrode configuration. When an electrode configuration is selected, stimulator device 22 may be configured such that no electrical energy is transmitted to the selected electrode configuration.

Next, processor 40 may be configured to transmit a control signal to stimulator device 22 to increase at least one parameter associated with the electrical stimulation pulse. Examples of such parameters may include, but are not limited to, amplitude of the electrical stimulation pulse, pulse polarity, pulse width, pulse shape, pauses or irregularities of pulses, frequency of stimulation, duty cycle, or the periodicity of stimulation. There may be gradual changes or sudden changes in such parameters over time. In the exemplary embodiment, processor 40 is configured to transmit a control signal to stimulator device 22 to increase an amplitude of the electrical stimulation pulse delivered by the selected electrode configuration. Processor 40 may be configured to increase the amplitude of the electrical stimulation pulse by a predetermined increment (step 56). The increment by which the amplitude is increased may be managed by the clinician. For example, the predetermined increment may be determined by the clinician prior to initiation of the algorithm (step 52). In the exemplary embodiment, the amplitude is increased by 0.1 mA; however, the amplitude may be increased by any other value.

Figure 5:
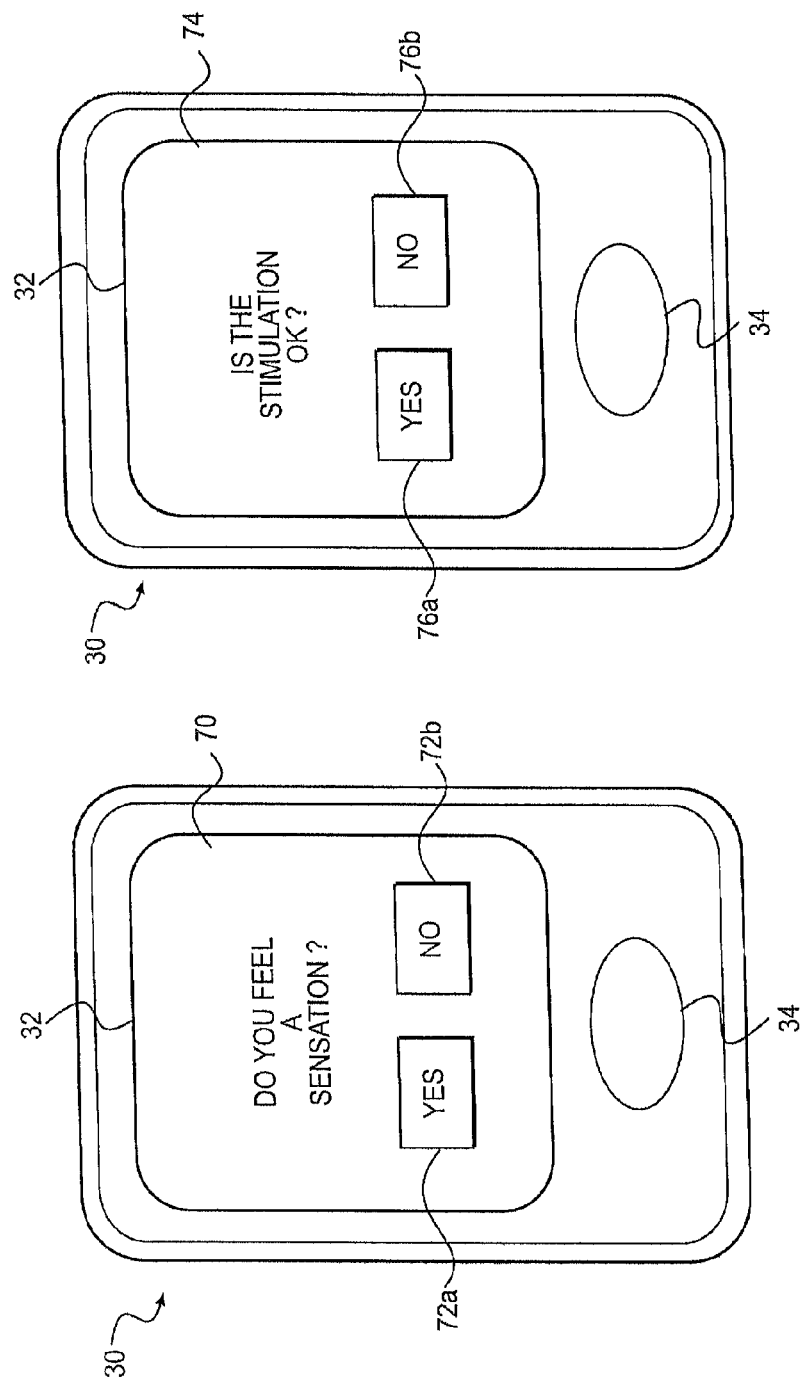
FIG. 5A is a representation of a graphical user interface (GUI) of the receiving device at step 58 of the method illustrated in FIG. 4, according to an embodiment of the disclosure.
FIG. 5B is a representation of a graphical user interface (GUI) of the receiving device at step 62 of the method illustrated in FIG. 4, according to an exemplary embodiment of the disclosure.

Processor 40 may then be configured to display on display 32 a user prompt. The user prompt may be a health care question to, for example, determine if the patient feels a sensation based on the increase in the amplitude of electrical stimulation (step 58). For example, a prompt 70 may be: "Do you feel a sensation?", as illustrated in FIG. 5A. In some embodiments, display 32 may include input graphical elements providing suggested responses. In the exemplary embodiment, the patient may be provided with graphical elements 72a, 72b providing "yes" or "no" response options. Patient feedback to prompt 70 may be entered via input device 34 by either the clinician or the patient. If the patient indicates feeling a sensation, the amplitude may be recorded and stored in memory 42 of receiving device 30 (step 60). If the patient indicates not feeling a sensation in response to prompt 70, the amplitude delivered by the selected electrode configuration may be increased until the patient indicates feeling a sensation. As an alternative to requiring patient input, processor 40 may wait 5 or 10 seconds, or any other appropriate time interval, before transmitting a signal to stimulator device 22 to increase the amplitude by the predetermined increment. The time interval may be shortened at low amplitude levels. In other embodiments, this determination may not be required.

After the patient indicates feeling a sensation, processor 40 may be configured to display on display 32 another user prompt. The user prompt may be a health care question to, for example, determine if the sensation is tolerable (step 62). For example, a prompt 77 may be: "Is the stimulation OK?", as illustrated in FIG. 5B. In the exemplary embodiment, the patient may also be provided with graphical elements 76a, 76b providing "yes" or "no" response options. Patient feedback to prompt 74 may be entered via input device 34 by either the clinician or the patient. If the patient indicates that the sensation is tolerable, the amplitude of electrical stimulation delivered by the selected electrode configuration may be increased until the patient indicates that the electrical stimulation is not tolerable (step 64). Once the patient indicates that the sensation is not tolerable, the amplitude may be recorded (step 66). Processor 40 may then switch to another electrode configuration and repeat the method until all electrode configurations have been exhausted (step 68).

In some embodiments, the method may be rendered more efficient by initially increasing the amplitude by substantially large increments (e.g., 0.5 mA) until the patient indicates that the sensation is not tolerable. Processor 40 may then generate and transmit a control signal to stimulator device 22 to reduce the amplitude delivered by the selected electrode configuration by, for example, 0.1 mA, until the patient indicates that the stimulation is tolerable. Alternatively, processor 40 may generate and transmit a control signal to stimulator device 22 to reset the amplitude delivered by the selected electrode configuration to the last setting and increase the amplitude by, for example, 0.1 mA, until the patient indicates that the stimulation is not tolerable. Additionally and/or alternatively, a clinician may manage the number of electrode configurations that are tested. For example, the clinician may prioritize or limit the electrode configurations to, for example, adjacent electrodes that are tested. In other embodiments, the clinician may initiate a contrast algorithm by which processor 40 runs the algorithm for a suspected "ideal" electrode configuration and a configuration expected to be substantially different to compare results.

After all of the electrode configurations have been tested, the results may be captured in a table for review by the clinician (step 69). An exemplary table 78 is illustrated in FIG. 6. Table 78 may list, for example, the electrode configurations, including the polarities of each electrode (wherein an anode is referenced as "A" and a cathode is referenced as "C"). In addition, for each tested electrode configuration, table 78 may include the recorded amplitude at which a sensation was felt and the recorded amplitude at which the patient indicated that the electrical stimulation was intolerable. Other parameters may also be included on table 78 such as, for example, the duration of stimulation, the frequency of stimulation, and the width of the electrical stimulation pulse. The clinician may then use table 78 to determine the most effective electrode configuration for delivering therapy by electrical stimulation. Criteria used for the determination may include, but is not limited to, the electrode configuration that generates the best efficacy measurement or lowest amplitude that meets a predetermined efficacy measurement threshold. The clinician may then input the parameters that identify the most effective electrode configuration into therapeutic program 48 to deliver therapy by electrical stimulation through the set of electrodes that meets the clinician's criteria.

In some embodiments, processor 40 automatically inputs these parameters into program 48. In those embodiments, processor 40 may be configured to display on display 32 a prompt requesting the clinician to input criteria by which to determine the most effective electrode configuration. Processor 40 may then add those parameters to therapeutic program 48.

Figure 7:
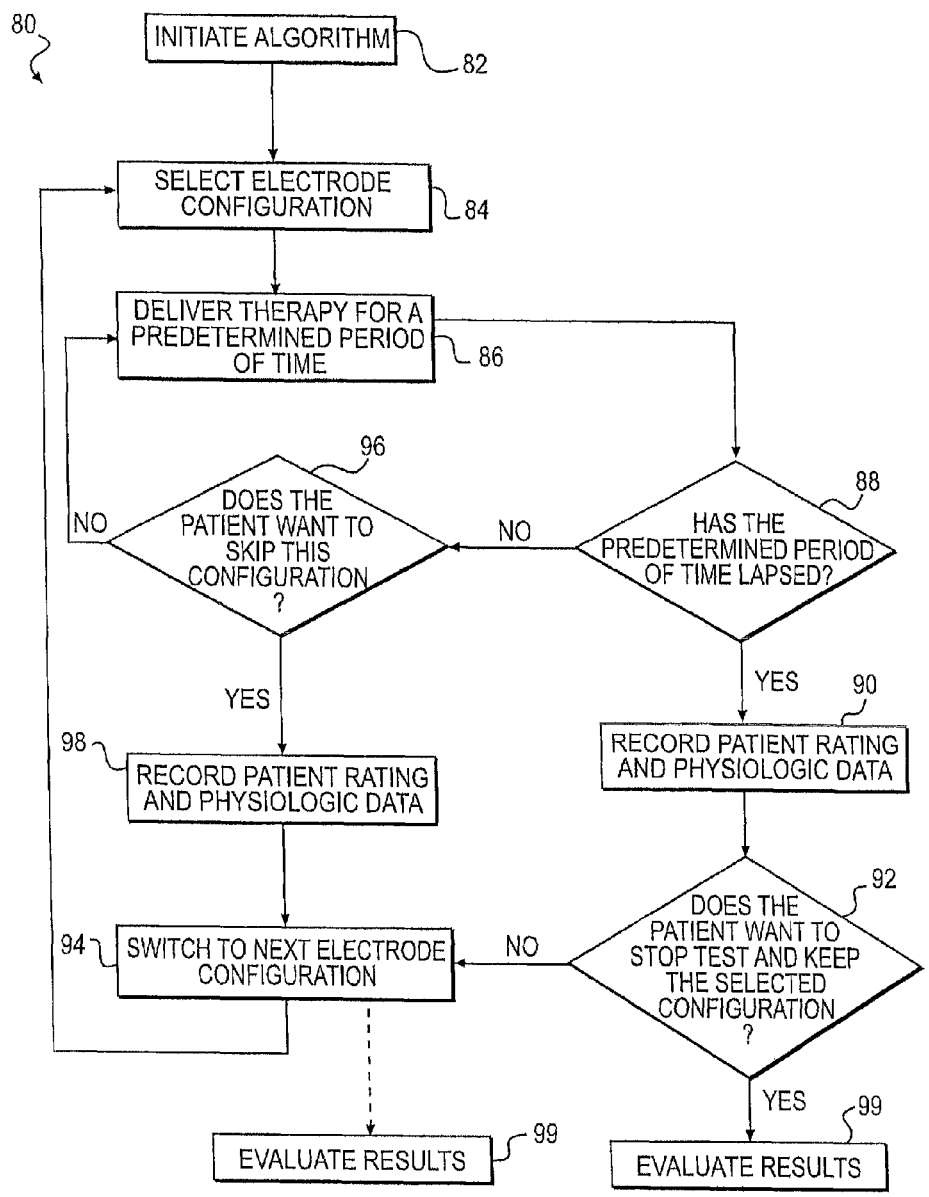
FIG. 7 is a flow diagram illustrating a method of determining an effective electrode configuration for delivery of therapy by electrical stimulation, according to another exemplary embodiment of the disclosure.

FIG. 7 illustrates another method for optimizing delivery of therapy by electrical stimulation. The exemplary method 80, illustrated in FIG. 7, may optimize delivery of therapy by a titration procedure to adjust therapy parameters including, for example, an effective electrode configuration and parameters associated with the electrode configuration. This method may be preferred for patients having chronic overactive bladder conditions. In accordance with this embodiment, an effective electrode configuration may be determined by testing an electrode configuration for a predetermined period of time until all the combinations of electrodes 26*a*-26*d* are exhausted. Processor 40 may then recommend or, alternatively, automatically program therapy by electrical stimulation for a patient through the set of electrodes that meets the clinician's efficacy criteria. This method may ease the clinician's service burden by giving patients more control over managing their therapy.

As illustrated, the method for optimizing delivery of therapy by electrical stimulation may begin when algorithm 46 associated with the method is initiated (step 82). In one embodiment, algorithm 46 may be initiated after stimulator device 22 has been implanted within the patient's body 10. It is contemplated that, in some circumstances, algorithm 46 may be initiated at a first programming session, or any subsequent follow-up visit, if appropriate. As discussed above, algorithm 46 may be initiated at a follow-up visit when, for example, it is believed that the position of one or more of the electrodes has changed, where accommodations to the therapy are required, or any other similar event. In some embodiments, the clinician, either in person or remotely, may initiate algorithm 46. In doing so, the clinician may input one or more parameters into the algorithm. For example, the clinician may program a maximum current for delivering electrical stimulation, an expected ideal electrode configuration, the number of electrode configurations to be tested, the amplitude of electrical stimulation delivered by the selected configurations, or any other relevant parameter (e.g., pulse width, frequency of pulses, duty cycles, or periodicity of stimulation). In some embodiments, the parameters may be determined by first performing the method illustrated in FIG. 4. In particular, the method illustrated in FIG. 4 may be performed to determine an ideal configuration, which may then be inputted for use during the method illustrated in FIG. 7.

Upon initiation of algorithm 46, an electrode configuration may be selected (step 84). The electrode configuration may be selected from the plurality of electrodes 26*a*-26*d* on lead 24. Each electrode configuration may be distinguished by the number of electrodes and, in some embodiments, the polarities of each electrode of the electrode configuration. When an electrode configuration is selected, stimulator device 22 may be configured such that no electrical energy is transmitted to the selected electrode configuration. Next, receiving device 30 may transmit a control signal to stimulator device 22 to deliver therapy by electrical stimulation through the selected electrode configuration for a predetermined period of time (step 86). In one example, the predetermined period of time may be a week, however, it will be understood that the predetermined period may be any suitable length of time.

Figure 8:
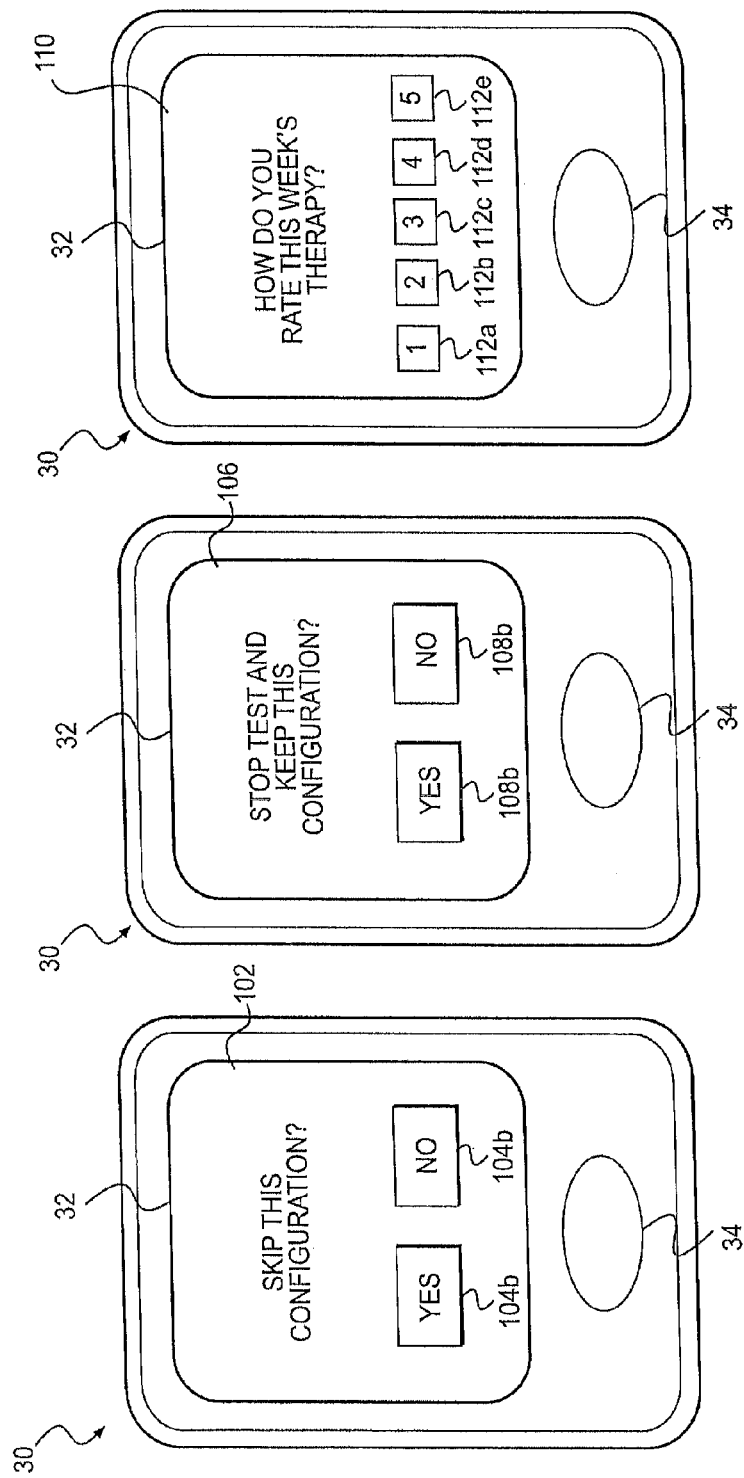
FIG. 8A is a representation of a graphical user interface (GUI) of the receiving device at step 96 of the method illustrated in FIG. 7, according to an embodiment of the disclosure.
FIG. 8B is a representation of a graphical user interface (GUI) of the receiving device at step 92 of the method illustrated in FIG. 7, according to an exemplary embodiment of the disclosure.
FIG. 8C is a representation of a graphical user interface (GUI) of the receiving device at steps 90 and 98 of the method illustrated in FIG. 7, according to an exemplary embodiment of the disclosure.

After processor 40 has determined that the predetermined period has lapsed (step 88), processor 40 may prompt the patient to evaluate the therapy. For example, processor 40 may be configured to display on display 32 a prompt 110: "How do you rate this week's therapy?", as illustrated in FIG. 8C. The patient may also be provided with graphical elements providing the suggested responses. In the exemplary embodiment, the patient may be provided with graphical elements 112*a*-112*e* providing a rating scale of 1-5. Patient feedback to prompt 110 may be entered via input device 34 by either the clinician or the patient.

Additionally and/or alternatively, processor 40 may receive signals from sensing element 28 and may record the data transmitted from sensing element 28. This data may include, but is not limited to, voiding frequency, bladder volume, bladder pressure, and/or any other physiologic data. Such data may be recorded separately or may be analyzed with the patient feedback to generate an automatic patient rating. The patient may then be provided with the option to terminate the method for optimizing delivery of therapy by electrical stimulation (step 92) or switch to the next electrode configuration (step 94) and repeat the method until all electrode configurations have been exhausted. To do so, processor 40 may be configured to display on display 32 a prompt 106, as illustrated in FIG. 8B, and may request a yes-or-no response as shown by graphical elements 108*a*, 108*b*.

In some embodiments, the patient may have the option to shorten the duration of therapy for an electrode configuration. In particular, processor 40 may be configured to display on display 32 a prompt over the course of the predetermined period, which may provide the patient with an option to skip the electrode configuration. An exemplary prompt 102 may be, for example, "Skip this configuration?", as illustrated in FIG. 8A, and may request a yes-or-no response as shown by graphical elements 104*a*, 104*b*. Input to prompt 102 may be entered via input device 34 by either the clinician or the patient. If the patient requests to skip the configuration, processor 40 may be configured to display on display 32 a prompt 110 requesting the patient to rate the therapy (step 98), before switching to the next electrode configuration (step 94).

After the desired electrode configurations have been tested, the results may be captured in a table for review by a clinician (step 99). An exemplary table is illustrated in FIG. 9. Table 112 may include, for example, the electrode configurations, including the polarities of each electrode (wherein an anode is referenced as "A" and a cathode is referenced as "C"). Table 112 further includes, for each electrode configuration, the amplitude at which a sensation was felt and the patient rating. Table 112 may also include other relevant parameters including, for example, pulse width, frequency of pulse, periodicity of therapy, and duration of therapy. The physician may then use table 112 to determine the most effective electrode configuration for delivering therapy by electrical stimulation. Criteria used for the determination may include, but is not limited to, the electrode configuration that generates the best efficacy measurement or lowest amplitude that meets a predetermined efficacy measurement threshold. The clinician may then program the therapeutic program to deliver therapy by electrical stimulation through the set of electrodes that meets the clinician's criteria. In alternate embodiments, processor 40 may automatically modify the diagnostic program to include such parameters and deliver the therapeutic electrical stimulation through the set of electrodes that meets the clinician's criteria.

Figure 10:
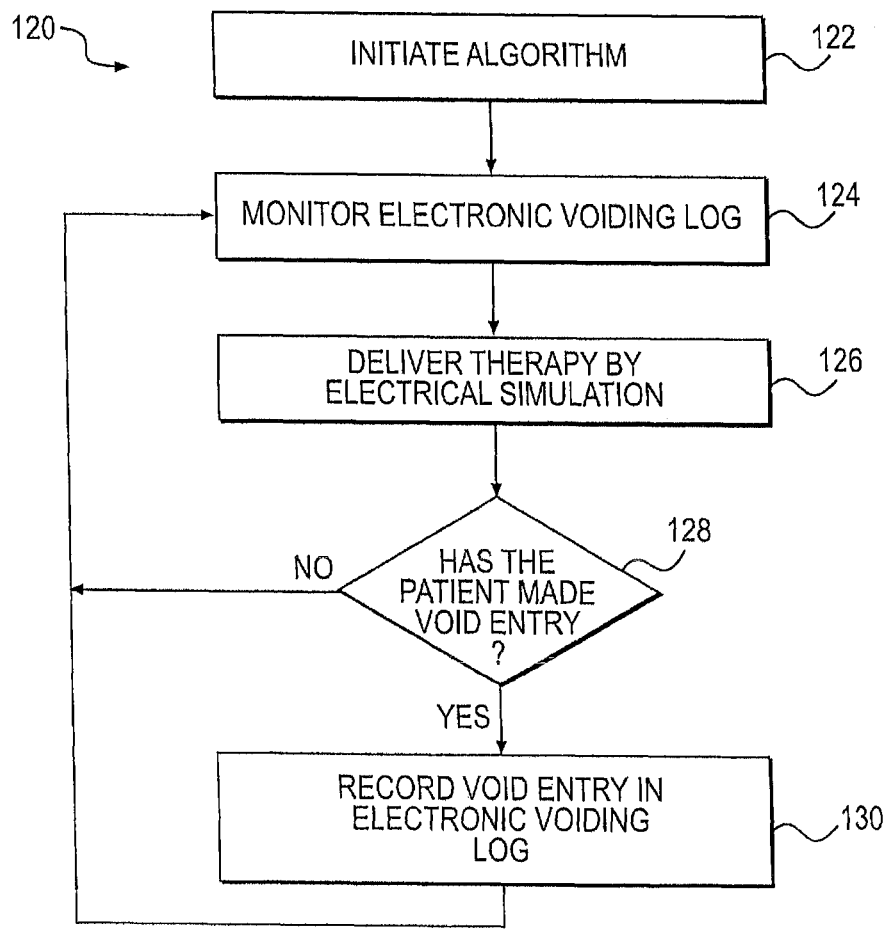
FIG. 10 is a flow diagram illustrating a method of monitoring voiding by a patient with overactive bladder syndrome, according to an exemplary embodiment of the disclosure.

FIG. 10 illustrates an exemplary method for monitoring voiding during the treatment of overactive bladder. Exemplary method 120 may be employed to capture the date and time of patient input of voiding so as to generate an electronic voiding log, which may improve the patient's treatment records and may ease the clinician's service burden by giving patients more control over their therapy.

As illustrated, exemplary method 120 may begin when algorithm 46 associated with the method is initiated (step 122). In one embodiment, algorithm 46 may be initiated after stimulator device 22 has been implanted within the patient's body 10. It is contemplated that, in some circumstances, algorithm 46 may be initiated at a first programming session.

Once algorithm 46 has been initiated, processor 40 may be configured to monitor an electronic voiding log stored in memory 42, including voiding entries (Step 124). Voiding entries refers to entries including the date and time of voiding by the patient. In some embodiments, the type of entry may correlate with the function of the bladder. For example, the input may indicate if the patient has voided voluntarily, or alternatively, if the patient has experienced leaking. Such data may be inputted manually through input device 34 or may be automatically detected via sensing element 28. When input is manually entered, the voiding entry may be confirmatory or may be merged with voiding entries that are recorded automatically.

Figure 11:
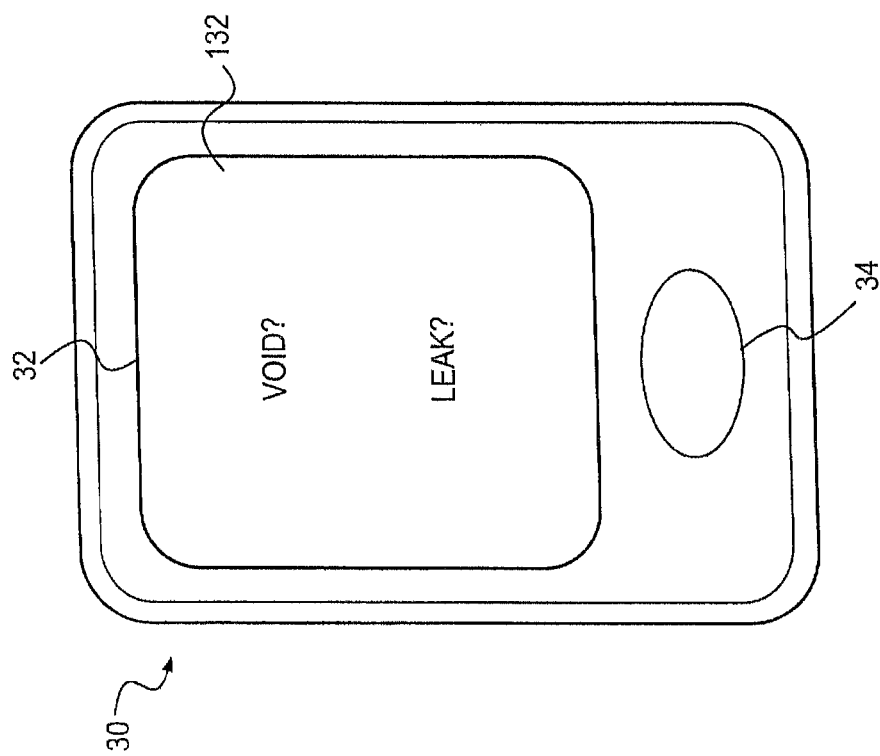
FIG. 11 is a representation of a graphical user interface (GUI) of the receiving device at step 128 of the method illustrated in FIG. 10, according to an exemplary embodiment of the disclosure.

As shown in FIG. 10, exemplary method 120 may include delivering electrical stimulation therapy (step 126). The electrical stimulation therapy may be optimized and delivered based on the methods described above. After delivering the therapy, processor 40 may compare signals received from sensing element 28 to the electronic voiding log to determine if the electronic voiding log has been modified and an entry regarding voiding has been made (step 128). In particular, processor 40 may analyze data received from sensing element 28 indicative of patient voiding and compare such data to the electronic log stored in memory 42. If an entry has not been made, processor 40 may be configured to display on display 32 prompts reminding the patient to enter data regarding the date and time of voiding. For example, processor 40 may be configured to display on display 32 a prompt 132, as illustrated in FIG. 11. If the entry has been made, processor 40 may record the information (step 130). Entries in the electronic voiding log may be analyzed, and an average of the entries and/or trends in the entries may be presented to the patient and/or clinician on receiving device 30 at a desktop communicator, a clinician programmer, or a remote programmer.

Figure 12:
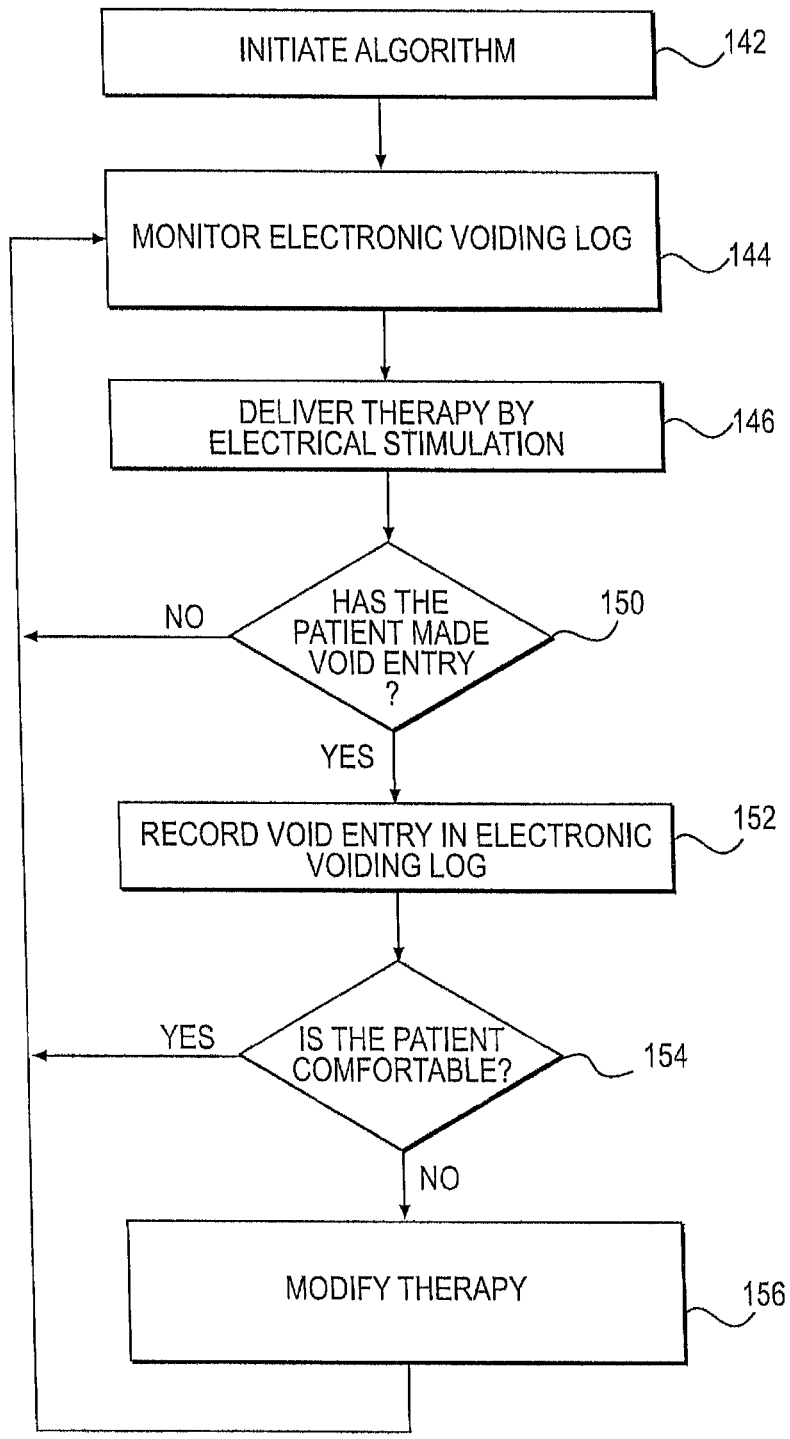
FIG. 12 is a flow diagram illustrating a method of monitoring voiding by a patient with overactive bladder syndrome, according to another exemplary embodiment of the disclosure.

FIG. 12 illustrates another exemplary method for monitoring voiding during the treatment of overactive bladder. As discussed above, the method may include initiating the algorithm (step 142) and monitoring the electronic voiding log (step 144) before and during delivery of therapy (step 146) by electrical stimulation. After delivery of therapy, processor 40 may be configured to display on display 32 a prompt to the patient requesting an input. For example, processor 40 may be configured to display on display 32 a prompt 158, as illustrated in FIG. 13A, reminding the patient to enter data regarding the date and time of voiding. If the entry has been made, processor 40 may record the information (step 152) and may further determine the if the patient is comfortable over the duration of treatment (step 154). For example, processor 40 may be configured to display on display 32 one or more questions designed to determine the patient's comfort levels. These questions may be yes-or-no questions, such as the exemplary prompt illustrated in FIG. 13B, or may require a rating that is analyzed by processor 40. Such questions may, for example, request that the patient identify if they are comfortable; rate their comfort level; identify if they perceive the urge to urinate has subsided or if the voiding frequency has increased or decreased; identify if they feel the electrical stimulation and, if so, identify if the sensation of stimulation is tolerable; identify if the perception of stimulation changes whether they are sitting or standing; and identify if they feel pain. If it is determined that the patient is comfortable, the processor may resume monitoring the voiding log. If it is determined that the patient is not comfortable, processor 40 may then modify the therapy (step 156). The modification of the therapy may include modifying the electrode configuration, and may be automatically executed by stimulator device 22 or receiving device 30. In other embodiments, receiving device 30 may alert a clinician, who may make such modifications by a clinician programmer or remotely by a desktop communicator.

In additional and/or alternative embodiments, the clinician may be able to program the duration and start time of the therapy by electrical stimulation. As therapy by electrical stimulation may be more comfortable during different times of the day or at different levels of activity, programming the duration and start time of the therapy by electrical stimulation may increase patient satisfaction over the duration of the treatment. As such, the clinician may be able to program a duration and set of start times, and the patient may be able to select the duration and/or the preferred start time. In some embodiments, the device may display a go button that initiates the automatic delivery of therapy. In other embodiments, the device may display a delay button that delays the automatic delivery of therapy. In some additional embodiments, the patient and/or clinician may be able to adjust for variations in the time zone or adjust for daylight savings. In yet other embodiments, the receiving device or a remote desktop communicator may automatically adjust start time based on a GPS or other knowledge.

In other embodiments, data entry into logs may further include environmental data about a patient that may affect a patient's response. Environmental data may include, but is not limited to, for example, food or drink consumption, the amount or quality of sleep, medications consumed, time of day, or exercise history. Such log entries could reflect patterns of environmental data or recent data history, for example, food consumption in the past 24 hours.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of optimizing the electrical stimulation of a bladder of a patient, the method comprising:
   selecting a first subset of electrodes from a set of electrodes positioned adjacent to nerves associated with the bladder, wherein each electrode of the set of electrodes is configured to deliver electrical stimulation pulses generated by a stimulator device to the nerves;
   delivering at least one electrical stimulation pulse through the first subset of electrodes;
   sensing a physiological response via a sensor positioned on an external bladder wall; and
   recording at least one parameter associated with the at least one electrical stimulation pulse delivered through the first subset of electrodes after receiving patient feedback and the physiological response.

2. The method of claim 1, wherein delivering at least one electrical stimulation pulse through the first subset of electrodes includes delivering the at least one electrical stimulation pulse for a predetermined period of time.

3. The method of claim 2, further including:
   determining a level of efficacy of electrical stimulation through the first subset of electrodes over the predetermined period of time based on patient feedback.

4. The method of claim 1, wherein recording at least one parameter includes recording a level of efficacy of electrical stimulation for the first subset of electrodes.

5. The method of claim 4, further including:
   adjusting the level of efficacy based on the one or more physiologic signals.

6. The method of claim 1, wherein sensing a physiological response includes sensing at least one of voiding frequency, bladder volume, and bladder pressure.

7. The method of claim 1, further including:
   selecting a second subset of electrodes different from the first subset of electrodes; and
   delivering at least one electrical stimulation pulse through the second subset of electrodes, wherein a magnitude of the at least one electrical stimulation pulse delivered through the first subset of electrodes is equal to a magnitude of the at least one electrical stimulation pulse delivered through the second subset of electrodes.

8. The method of claim 7, further including:
   recording at least one parameter associated with the at least one electrical stimulation pulse delivered through the second subset of electrodes after receiving patient feedback.

9. The method of claim 8, further including:
   comparing the recorded at least one parameter associated with the at least one electrical stimulation pulse of the first subset of electrodes to the recorded at least one parameter associated with the at least one electrical stimulation pulse of the second subset of electrodes to determine the relative efficacy of each of the first subset of electrodes and the second subset of electrodes.

10. The method of claim 1, further including:
    repeating the selecting, delivering, sensing, and recording steps with all combinations of electrodes of the set of electrodes.

11. The method of claim 1, wherein the sensor positioned on an external bladder wall includes at least one of a chemical, an electrical, and a mechanical sensor.

12. A method of optimizing the electrical stimulation of a bladder of a patient, the method comprising:
    selecting a first subset of electrodes from a set of electrodes positioned adjacent to nerves associated with the bladder, wherein each electrode of the set of electrodes is configured to deliver electrical stimulation pulses generated by a stimulator device to the nerves;
    delivering at least one electrical stimulation pulse through the first subset of electrodes;
    recording at least one parameter associated with the at least one electrical stimulation pulse delivered through the first subset of electrodes after receiving patient feedback; and
    repeating the selecting, delivering, and recording steps with all combinations of electrodes of the set of electrodes.

13. The method of claim 12, further including:
    selecting a second subset of electrodes different from the first subset of electrodes; and
    delivering at least one electrical stimulation pulse through the second subset of electrodes, wherein a magnitude of the at least one electrical stimulation pulse delivered through the first subset of electrodes is equal to a magnitude of the at least one electrical stimulation pulse delivered through the second subset of electrodes.

14. The method of claim 13, further including:
    recording at least one parameter associated with the at least one electrical stimulation pulse delivered through the second subset of electrodes after receiving patient feedback.

15. The method of claim 14, further including:
    comparing the recorded at least one parameter associated with the at least one electrical stimulation pulse of the first subset of electrodes to the recorded at least one parameter associated with the at least one electrical stimulation pulse of the second subset of electrodes to determine the relative efficacy of each of the first subset of electrodes and the second subset of electrodes.

16. The method of claim 12, further including:
    sensing a physiological response via a sensor positioned on an external bladder wall.

17. The method of claim 16, wherein sensing a physiological response includes sensing at least one of voiding frequency, bladder volume, and bladder pressure.

18. The method of claim 16, wherein the sensor positioned on an external bladder wall includes at least one of a chemical, an electrical, and a mechanical sensor.

19. The method of claim 12, wherein recording of at least one parameter includes recording a level of efficacy of electrical stimulation for the first subset of electrodes.

20. A method of optimizing the electrical stimulation of a bladder of a patient, the method comprising:
    selecting a first subset of electrodes from a set of electrodes positioned adjacent to nerves associated with the bladder, wherein each electrode of the set of electrodes is configured to deliver electrical stimulation pulses generated by a stimulator device to the nerves;
    delivering at least one electrical stimulation pulse through the first subset of electrodes;
    sensing a physiological response via a sensor positioned on an external bladder wall; and
    recording at least one parameter associated with the at least one electrical stimulation pulse delivered through the first subset of electrodes after receiving patient feedback and the physiological response
    wherein the sensor positioned on an external bladder wall includes at least one of a chemical, an electrical, and a mechanical sensor.

* * * * *